United States Patent [19]

Jensen

[11] 3,932,439

[45] Jan. 13, 1976

[54] N-SUBSTITUTED CYCLOSERINE COMPOUNDS, SALTS THEREOF, AND PROCESSES FOR PREPARING THEM

[75] Inventor: Norman P. Jensen, Watchung, N.J.

[73] Assignee: Merck & Co., Inc., Rahway, N.J.

[22] Filed: May 28, 1974

[21] Appl. No.: 473,164

Related U.S. Application Data

[63] Continuation-in-part of Ser. No. 384,545, Aug. 1, 1973, abandoned.

[52] U.S. Cl............................. 260/307 A; 260/999
[51] Int. Cl.²...................................... C07D 261/04
[58] Field of Search.............................. 260/307 A

[56] References Cited
UNITED STATES PATENTS 2,773,878   12/1956   Shull et al........................... 260/307

*Primary Examiner*—Raymond V. Rush
*Attorney, Agent, or Firm*—J. Jerome Behan; Henry H. Bassford, Jr.

[57] ABSTRACT

Stabilized cycloserine compositions, having enhanced stability, and effective in releasing cycloserine compounds in vivo, are prepared by reacting D-4-amino-3-isoxazolidinone or its 5-methyl derivative with 2,4-pentanedione or alkyl-substituted-2,4-pentanedione to form the corresponding N-substituted-cycloserine compound in which one of the hydrogens attached to the primary amino group is replaced by 1-methyl-3-oxo-1-butenyl or an alkyl substituted-1-methyl-3-oxo-1-butenyl grouping. These D-4-(1'-methyl-3'-oxo-1'-butenyl or alkyl-substituted-1'-methyl-3'-oxo-1'-butenyl)amino-3-isoxazolidinones or 5-methyl derivative thereof, which may also be referred to as N-(1-methyl-3-oxo-1-butenyl or alkyl-substituted-1-methyl-3-oxo-1-butenyl)-derivative of cycloserine or methyl-cycloserine, as well as their pharmacologically acceptable salts, are remarkably stable on storage as well as upon oral administration, and are extremely effective in releasing in vivo the cycloserine compound containing the free primary amino grouping.

16 Claims, No Drawings

N-SUBSTITUTED CYCLOSERINE COMPOUNDS, SALTS THEREOF, AND PROCESSES FOR PREPARING THEM

This is a continuation-in-part of application Ser. No. 384,545, filed Aug. 1, 1973, now abandoned.

This invention is concerned generally with N-substituted cycloserine compositions, which may be represented by the following formula:

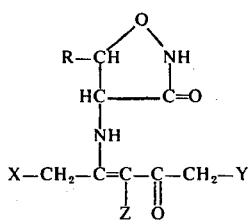

wherein R is hydrogen or methyl, and X, Y and Z are hydrogen or alkyl, and pharmacologically acceptable salts thereof. These presently invented N-(1-methyl-3-oxo-1-butenyl or alkyl-substituted-1-methyl-3-oxo-1-butenyl)cycloserine (or methyl-cycloserine) compositions, which may also be referred to as D-4-(1'-methyl-3'-oxo-1'-butenyl or alkyl-substituted-1'-methyl-3'-oxo-1'-butenyl)amino-3-isoxazolidinones or 5-methyl derivatives thereof, include D-4-(1'-methyl-3'-oxo-1'-butenyl)amino-3-isoxazolidinone, D-4-(1'-methyl-3'-oxo-1'-butenyl)amino-5-methyl-3-isoxazolidinone, D-4-(1',2'-dimethyl-3'-oxo-1'-butenyl)amino-3-isoxazolidinone, D-4-(1',2'-dimethyl-3'-oxo-1'-butenyl)amino-5-methyl-3-isoxazolidinone, D-4-(1'-ethyl-3'-oxo-1'-butenyl)amino-5-methyl-3-isoxazolidinone, D-4-(1'-ethyl-2'-methyl-3'-oxo-1'-butenyl)amino-3-isoxazolidinone, D-4-(1'-ethyl-2'-methyl-3'-oxo-1'-butenyl)amino-5-methyl-3-isoxazolidinone, D-4-(1'-ethyl-3'-oxo-1'-pentenyl)amino-3-isoxazolidinone, D-4-(1'-ethyl-3'-oxo-1'-pentenyl)amino-5-methyl-3-isoxazolidinone, D-4-(1'-ethyl-2'-methyl-3'-oxo-1'-pentenyl)amino-3-isoxazolidinone, D-4-(1'-ethyl-2'-methyl-3'-oxo-1'-pentenyl)-amino-5-methyl-3-isoxazolidinone, D-4-(1'-ethyl-3'-oxo-1'-butenyl)amino-3-isoxazolidinone, and the like; pharmacologically acceptable salts of the foregoing such as alkali metal salts, preferably the sodium and potassium salts; alkaline earth metal salts preferably the calcium and magnesium salts; ammonium salts; amine salts, preferably salts with triethylamine, diethylamine, N-methyl glucamine, diethanolamine, triethanolamine or 2-amino-2-hydroxymethyl-1,3-propanediol, and the like, as for example, the sodium salt of D-4-(1'-methyl-3'-oxo-1'-butenyl)amino-3-isoxazolidinone, the potassium salt of D-4-(1'-methyl-3'-oxo-1'-butenyl)amino-3-isoxazolidinone, the ammonium salt of D-4-(1'-methyl-3'-oxo-1'-butenyl)amino-3-isoxazolidinone, the calcium salt of D-4-(1'-methyl-3'-oxo-1'-butenyl)amino-3-isoxazolidinone, the sodium salt of D-4-(1'-methyl-3'-oxo-1'-butenyl)amino-5-methyl-3-isoxazolidinone, and the like. These N-(1-methyl13-oxo-1-butenyl or alkyl-substituted-1-methyl-3-oxo-1-butenyl)derivatives of cycloserine or methyl-cycloserine compounds, their pharmacologically acceptable salts and, more particularly, D-4-(1'-methyl-3'-oxo-1'-butenyl)amino-3-isoxazolidinone and D-4-(1',2'-dimethyl-3'-oxo-1'-butenyl)amino-3-isoxazolidinone, and their sodium and potassium salts, are remarkably stable in aqueous solution; when administered orally, they are extremely effective in releasing cycloserine or methyl-cycloserine in the blood stream and in the bladder and, at the same time, substantially avoiding the unwanted dimerization of the cycloserine or methyl-cycloserine.

These new N-(1-methyl-3-oxo-1-butenyl or alkyl-substituted-1-methyl-3-oxo-1-butenyl) derivatives of cycloserine or methyl-cycloserine compounds are prepared, in accordance with the present invention, by reacting cycloserine or methyl-cycloserine with a 2,4-pentanedione compound having the following formula:

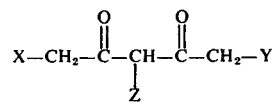

wherein X, Y and Z are hydrogen or alkyl, such as 2,4-pentanedione, 3-methyl-2,4-pentanedione, 2,4-hexanedione, 3-methyl-2,4-hexanedione, 3,5-heptanedione, 4-methyl-3,5-heptanedione, and the like. The reaction between the cycloserine or methylcycloserine and the 2,4-pentanedione compound is ordinarily conducted by intimately contacting a mixture of the cycloserine compound and 2,4-pentanedione compound. Although the reaction can be carried out, if desired, in the presence of an organic liquid which is miscible with the 2,4-pentanedione compound, such as diethyl ether, it is ordinarily preferred to stir together a mixture of the cycloserine compound and an excess of the 2,4-pentanedione compound whereby the latter acts both as reactant and as reaction medium. Under these latter reaction conditions, the cycloserine compound gradually goes into solution, with formation of the corresponding N-substituted-cycloserine compound which, as the reaction proceeds, ordinarily crystallizes from the resulting reaction solution. It is ordinarily preferred to conduct the reaction under substantially anhydrous conditions. Temperatures from about 0°C to about 35°C may be employed, if desired; but, at temperatures substantially above about room temperature, reduced yield and unwanted by-products may result and, at temperatures of about 0°C, the reaction time is substantially increased. Accordingly, it is preferred to carry out the reaction at approximately room temperature, at which temperature the reaction is ordinarily complete in about 40–48 hours.

The N-substituted-cycloserine compound which, as previously indicated, ordinarily crystallizes from the reaction solution, is conveniently recovered by filtration or centrifugation, washed with an organic solvent such as diethyl ether, and dried, preferably at room temperature in vacuo, to give the said N-substituted-cycloserine compound of the formula:

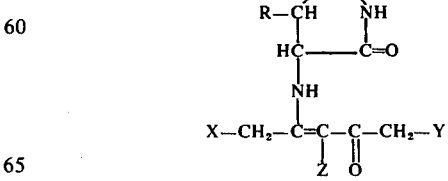

wherein R is hydrogen or methyl, and X, Y and Z are hydrogen or alkyl, in substantially pure form.

The N-substituted-cycloserine compound is ordinarily converted to its salts by reacting the N-substituted-cycloserine with the appropriate base, such as sodium methoxide, potassium methoxide, ammonia, or an amine in a solution in a lower alkanol such as methanol or ethanol, sodium hydroxide or potassium hydroxide in solution in a lower alkanol such as methanol, or with sodium hydroxide, potassium hydroxide, calcium oxide or magnesium oxide in aqueous solution; when the reaction is conducted in aqueous solution, the alkali or alkaline earth metal salt of the N-substituted-cycloserine compound is conveniently precipitated by the addition of a lower alkanol such as ethanol to the aqueous reaction solution.

The following examples illustrate methods of carrying out the present invention, but it is to be understood that these examples are give for purposes of illustration and not of limitation.

EXAMPLE 1

A mixture of about 3.0 g. of D-4-amino-3-isoxazolidinone and 30 ml. of 2,4-pentanedione is stirred in a dry atmosphere at approximately room temperature for about 2 days. The D-4-amino-3-isoxazolidinone gradually goes into solution; and the reaction product, which crystallizes from the reaction solution, is recovered by filtration, washed with three 20 ml.-portions of ether, and dried at room temperature in vacuo to give about 3.5 g. of D-4-(1'-methyl-3'-oxo-1'-butenyl)amino-3-isoxazolidinone; m.p. 145°C. dec.; $\alpha_D^{27} = -159°$ (1% methanol).

EXAMPLE 2

A mixture of about 3.0 g. of D-4-amino-5-methyl-3-isoxazolidinone and 30 ml. of 2,4-pentanedione is stirred in a dry atmosphere at approximately room temperature for a period of about 2 days. The D-4-amino-5-methyl-3-isoxazolidinone gradually dissolves; and the reaction product, which crystallizes from the reaction solution, is recovered by filtration, washed with three 20 ml.-portions of ether, and dried at room temperature in vacuo to give about 3.5 g. of D-4-(1'-methyl-3'-oxo-1'-butenyl)amino-5-methyl-3-isoxazolidinone.

EXAMPLE 3

A mixture of about 2.0 g. of D-4-amino-3-isoxazolidinone and 10 ml. of 3-methyl-2,4-pentanedione is stirred in a dry atmosphere at approximately room temperature for a period of about 42 hours. The D-4-amino-3-isoxazolidinone gradually goes into solution; and the reaction product, which crystallizes from the reaction solution, is recovered by filtration, washed with five 5 ml.-portions of ether, and dried at room temperature in vacuo to give about 2.0 g. of D-4-(1',2'-dimethyl-3'-oxo-1'-butenyl)amino-3-isoxazolidinone; m.p. 121.5°–123.5°C.

EXAMPLE 4

A mixture of about 2.0 g. of D-4-amino-5-methyl-3-isoxazolidinone and 10 ml. of 3-methyl-2,4-pentanedione is stirred in a dry atmosphere at about room temperature for a period of about 42 hours. The D-4-amino-5-methyl-3-isoxazolidinone gradually goes into solution; and the reaction product, which crystallizes from the reaction solution, is recovered by filtration, washed with five 5 ml.-portions of ether, and dried at room temperature in vacuo to give about 2.0 g. of D-4-(1',2'-dimethyl-3'-oxo-1'-butenyl)amino-5-methyl-3-isoxazolidinone.

EXAMPLE 5

About 0.143 g. of D-4-(1'-methyl-3'-oxo-1'-butenyl)amino-3-isoxazolidinone is dissolved in 0.3 ml. of methanol, and 1.56 ml. of an 0.50 molar solution of sodium hydroxide in methanol is added to give a pH of approximately 7.0. The methanol is evaporated from the resulting solution under a stream of nitrogen until crystals form, and the crystalline slurry is further evaporated to dryness in vacuo to give approximately 0.16 g. of residual material. An 0.152 gram portion of this residual material is washed with 2.5 ml. of acetone, and redissolved in 0.55 ml. of methanol; the solution is filtered and the filtrate diluted with 0.45 ml. of methanol. To the resulting solution is added 4 ml. of ether, and the crystalline precipitate which forms is recovered by filtration, washed with ether and dried to give about 0.13 g. of D-4-(1'-methyl-3'-oxo-1'-butenyl)amino-3-isoxazolidinone sodium salt-hemihydrate; m.p. 186°–188°C.

EXAMPLE 6

About 3.0 g. of calcium oxide is slurried in 40 ml. of water, and the slurry is cooled to 0°–5°C. About 5 g. of D-4-(1'-methyl-3'-oxo-1'-butenyl)amino-3-isoxazolidinone is added to the cooled slurry, and the resulting mixture is heated with stirring to room temperature, and stirred at that temperature for about 5 minutes. The mixture is filtered, and the insoluble material is washed with 10 ml. of water. To the combined solution and washings (having a pH of about 11.0 – 11.5) is added sufficient D-4-(1'-methyl-3'-oxo-1'-butenyl)amino-3-isoxazolidinone to give a final pH of about 9.5. Activated carbon (0.5 g.) is added to the resulting solution, and the mixture is stirred for about 15 minutes and filtered. The filtered solution is diluted with six times its volume of ethanol, and the crystalline precipitate which forms is recovered by filtration, washed with isopropanol and dried in vacuo to give, in substantially pure form, the calcium salt of D-4-(1'-methyl-3'-oxo-1'-butenyl) amino-3-isoxazolidinone.

Various changes and modifications may be made in carrying out the present invention without departing from the spirit and scope thereof. Insofar as these changes and modifications are within the purview of the annexed claims, they are to be considered as part of this invention.

What is claimed is:

1. A process which comprises the step of reacting, at a temperature of about 0° to 35°C., a cycloserine compound having the formula

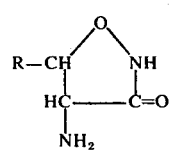

wherein R is hydrogen or methyl with 2,4-pentanedione, or derivatives thereof, having the formula:

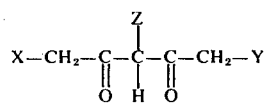

wherein X, Y and Z are hydrogen or methyl thereby forming the corresponding N-substituted cycloserine compound having the formula:

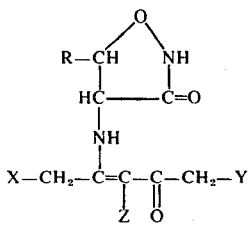

wherein R, X, Y and Z have the significance above-defined.

2. A process as defined in claim 1 wherein the N-substituted cycloserine compound is reacted with a nontoxic base to form the corresponding pharmacologically acceptable salt.

3. A process as defined in claim 1 which comprises the step of reacting D-4-amino-3-isoxazolidinone with 2,4-pentanedione thereby forming D-4-(1′-methyl-3′-oxo-1′-butenyl)amino-3-isoxazolidinone.

4. A process as defined in claim 2 wherein D-4-(1′-methyl-3′-oxo-1′-butenyl) amino-3-isoxazolidinone is reacted with an alkali metal or alkaline earth metal hydroxide or alkoxide, ammonia, triethylamine, diethylamine, N-methyl glucamine, diethanolamine, triethanolamine or 2-amino-2-hydroxymethyl-1,3-propanediol, to form the corresponding salt of D-4-(1′-methyl-3′-oxo-1′-butenyl)amino-3-isoxazolidinone.

5. The process which comprises the step of reacting D-4-(1′-methyl-3′-oxo-1′-butenyl)amino-3-isoxazolidinone with sodium hydroxide in methanol thereby forming D-4-(1′-methyl-3′-oxo-1′-butenyl)amino-3-isoxazolidinone sodium salt-hemihydrate.

6. A process as defined in claim 1 which comprises the step of reacting D-4-amino-5-methyl-3-isoxazolidinone with 2,4-pentanedione thereby forming D-4-(1′-methyl-3′-oxo-1′-butenyl)amino-5-methyl-3-isoxazolidinone.

7. A process as defined in claim 1 which comprises the step of reacting D-4-amino-3-isoxazolidinone with 3-methyl-2,4-pentanedione thereby forming D-4-(1′,2′-dimethyl-3′-oxo-1′-butenyl)amino-3-isoxazolidinone.

8. A process as defined in claim 1 which comprises the step of reacting D-4-amino-5-methyl-3-isoxazolidinone with 3-methyl-2,4-pentanedione thereby forming D-4-(1′,2′-dimethyl-3′-oxo-1′-butenyl)amino-5-methyl-3-isoxazolidinone.

9. An N-substituted cycloserine compound having the formula

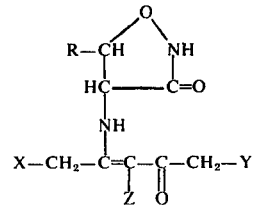

wherein R is hydrogen or methyl, and X, Y and Z are hydrogen or methyl, and pharmacologically acceptable salts thereof.

10. D-4-(1′-methyl-3′-oxo-1′-butenyl)amino-3-isoxazolidinone and pharmacologically acceptable salts thereof.

11. D-4-(1′-methyl-3′-oxo-1′-butenyl)amino-3-isoxazolidinone.

12. D-4-(1′-methyl-3′-oxo-1′-butenyl)amino-3-isoxazolidinone sodium salt-hemihydrate.

13. Calcium salt of D-4-(1′-methyl-3′-oxo-1′-butenyl)amino-3-isoxazolidinone.

14. A compound as defined in claim 9 having the chemical name D-4-(1′-methyl-3′-oxo-1′-butenyl)amino-5-methyl-3-isoxazolidinone.

15. A compound as defined in claim 9 having the chemical name D-4-(1′,2′-dimethyl-3′-oxo-1′-butenyl)amino-3-isoxazolidinone.

16. A compound as defined in claim 9 having the chemical name D-4-(1′,2′-dimethyl-3′-oxo-1′-butenyl)amino-5-methyl-3-isoxazolidinone.

* * * * *